Figure 1:
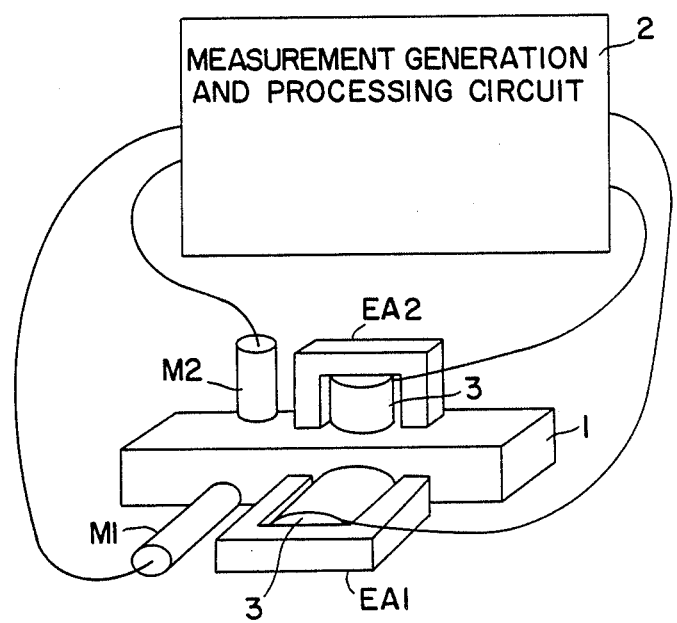

United States Patent [19]

Michel

[11] Patent Number: 4,829,823

[45] Date of Patent: May 16, 1989

[54] APPARATUS FOR DETECTING DEFECTS, PARTICULARLY IN CASTINGS

[76] Inventor: Jacob Michel, 15 rue du Sel, 56700 Hennebont, France

[21] Appl. No.: 98,622

[22] PCT Filed: Dec. 26, 1986

[86] PCT No.: PCT/FR86/00447

§ 371 Date: Aug. 14, 1987

§ 102(e) Date: Aug. 14, 1987

[87] PCT Pub. No.: WO87/04250

PCT Pub. Date: Jul. 16, 1987

[30] Foreign Application Priority Data

Dec. 27, 1985 [FR] France ................. 85 19454

[51] Int. Cl.⁴ .................................................. G01N 29/00
[52] U.S. Cl. .................................................. 73/579
[58] Field of Search ................. 73/579, 580, 581, 582, 73/583, 598, 602, 649, 657

[56] References Cited

U.S. PATENT DOCUMENTS 4,122,723 10/1978 Levizzari et al. ................. 73/579
4,297,884 11/1981 Leveque et al. ................. 73/579

FOREIGN PATENT DOCUMENTS 492802 6/1976 U.S.S.R. ................. 73/579

Primary Examiner—Stewart J. Levy
Assistant Examiner—Louis M. Arana
Attorney, Agent, or Firm—Roland Plottel

[57] ABSTRACT

An apparatus for detecting defects in workpieces, particularly in foundry or metallurgical workpieces, including a plurality of means for exciting and picking up the vibrations emitted by a workpiece, whose sound resonance frequencies it is desired to measure so as to evaluate the quality thereof.

5 Claims, 2 Drawing Sheets

APPARATUS FOR DETECTING DEFECTS, PARTICULARLY IN CASTINGS

The present invention relates to an apparatus for detecting faults in workpieces, particularly in foundry, metallurgical workpieces etc so that, after manufacture, the workpieces having faults which are too great can be sorted out. The apparatus detects the material faults which have an influence on the elasticity of the material such as the nodularity rate variations of the spheroidal graphite melts or the thermal treatments, the overall defects of geometry due for example to the opening, to the wear or to the offcentering of the molds, localized defects such as cracks, shrinkage holes . . .

Several techniques already exist for providing such detection. There exist for example systems for testing work pieces by resonance which use a hammer which strikes the work piece, the sound picked up by a micrphone or by induction in a solenoid is then filtered so as to select one of the resonance frequencies from the set of frequencies characteristic of the work piece, this frequency is then compared with a given threshold.

Since the resonance frequencies depend on variables such as the characteristics of the material (coefficient of elasticity and density), shapes or dimensions of the work piece and pin point defects, a method such as the one which has just been described which only uses a single one of the resonance freqeuencies does not allow the different variables to be determined, since a single equation is obtained with several unknowns.

Furthermore, the method which consists in energizing the work piece by shocks so as to analyse the spectrum thereof has the drawback of being difficult to use in the work shop for the signal to be analysed is greatly disturbed by the ambient speech and noises, and it is difficult to mesure the resonance frequencies with a low overvoltage, for this technique would require analysis of the signal by Fourier transform for example which would be long and expensive in order to obtain the required precision.

Considering the interest shown by constructors in having a reliable, rapid and automatable testing tool, the purpose of the invention is to provide apparatus overcoming the different above mentioned drawbacks, by successively exciting the different resonances characteristic of the work piece so as to measure the frequency thereof and possibly the over voltage and by processing the data collected which leads to obtaining the different characteristics of the work piece, The invention relates more precisely to an apparatus for detecting defects in work pieces, particularly in foundry or metallurgical work pieces, including a plurality of pairs for exciting and picking up the vibrations emitted by a work piece, whose sound resonance frequencies it is desired to measure so as to evaluate the quality thereof.

Figure 2:
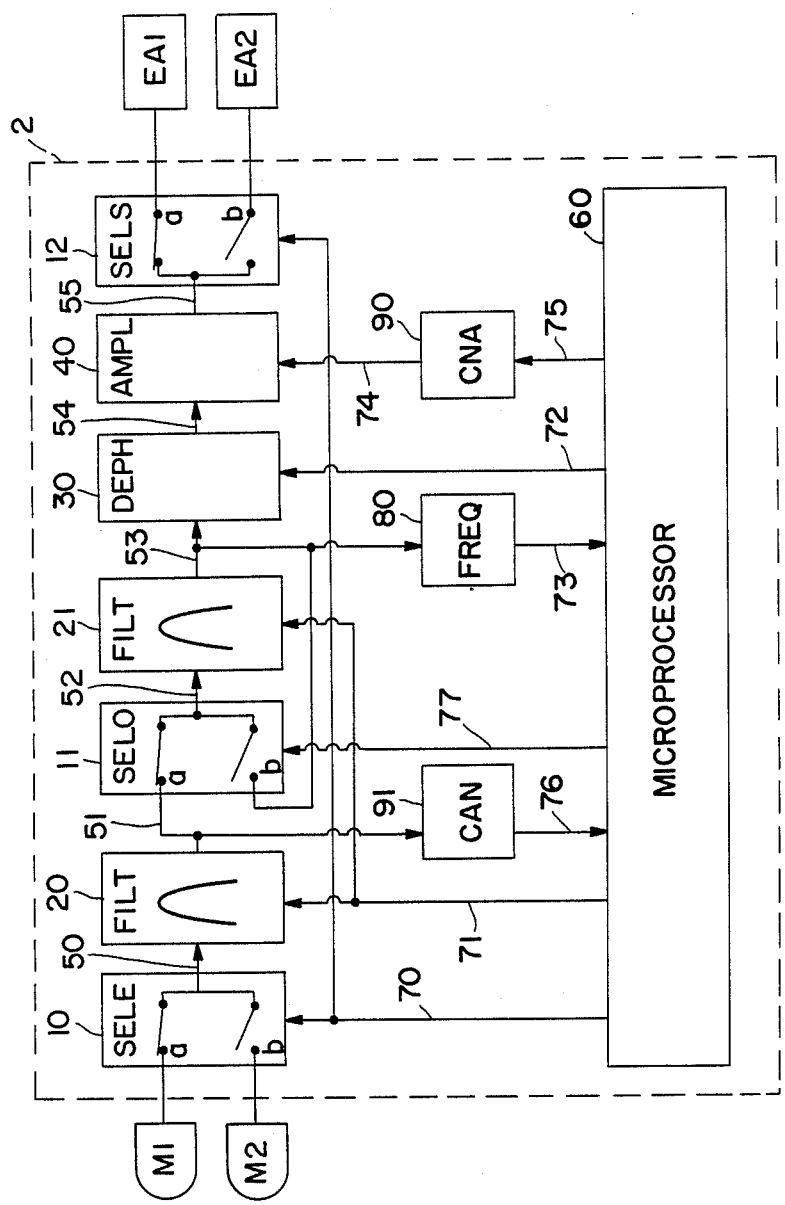

The invention will be better understood from the following explanations and the accompanying Figs. in which:

FIG. 1 illustrates schematically an apparatus in accordance with the invention, and FIG. 2 is a diagram illustrating a measurement generation and processing circuit in accordance with the invention. For greater clarity, the same elements bear the same references throughout the Figs.

As shown in FIG. 1, vibration exciting and sensing pairs are disposed close to the work piece 1 to be tested, for example (EA1, M1 and EA2, M2).

The exciters EA1, EA2 and sensors M1, M2 are connected to a measurement generation and processing circuit 2. In this example, only two exciting and sensing pairs are shown which allow, for example, the vertical vibration modes to be measured for EA2 and the horizontal modes for EA1, but it is possible to extend the method by adding other pairs so as to obtain rotational resonsance modes for example.

Work piece 1 is laid on a support (not shown), and preferably made from a resilient material which does not damp the vibrations, so that the position of the support with respect to the vibration nodes becomes less critical.

In the example described, exciter EA1 and/or EA2 is an electromagnet whose coil 3 has a current flowing therethrough, the vibration sensor M1 and/or M2 is a microphone, but any other mechanical excitation device and any other vibration sensor is suitable, all the more so since the exciter and the sensor do not use the same physical phenomenon so as to avoid direct coupling between the exciter and the sensor. In one example which is in no way limitative, a magnetic sensor and an electric microphone may be used.

Several electromagnetics are disposed at given positions close to the work piece 1, these positions are vibration antinodes, so as to obtain the maximum of mechanical resonance modes and so as to have the maximum independent information concerning this work piece 1. Each sensor M1 and/or M2 is disposed as close as possible to the exciter with which it is associated and in the same direction.

So as to obtain a maximum of measurements in the minimum of time with the highest possible accuracy and the greatest insensitivity to ambient noises, the work piece 1 is used as an element for checking the frequency of an oscillator whose frequency is measured. Two pairs (EA1, M1) and (EA2, M2) are here described but as was mentioned above, this number of pairs may be increased. As shown in FIG. 2, which is the illustration of the measurement generation and processing circuit 2 of FIG. 1, this oscillator is formed of the work piece 1 to be tested (not shown in FIG. 1), which behaves like a set of narrow pass band filters, which are stimulated to vibrate at a given time at one of the frequencies, the vibration is picked up by one of the sensors (M1 or M2) selected by an input selector SELE (10) according to whether the input terminal (A) or the terminal (B) is selected. The output 50 of the selector SELE 10 is connected to a programmable filter FILT 20 whose pass band is sufficiently wide with respect to that of the work piece 1 so as not to influence the measurement thereof. The output 51 of filter 20 is connected to the input terminal A of the selector SELO 11 whose output 52 is connected to the input of a filter FILT 21 of the same type as filter FILT 20. The output 53 of the filter FILT 21 is connected to the input of a programmable phase shifter DEPH 30 whose output 54 is connected to a level programmable power amplifier AMPL 40. The output 55 of this amplifier is connected to the input of an output selector SELS 12, whose output terminal a is connected to the exciter EA1, the second output terminal b being connected to the exciter EA2.

In FIG. 2 has been shown the case where the selectors SELE 10 and SELS 12 select respectively the sensor M1 and the exciter EA1 which causes the work piece 1 to vibrate, the vibration picked up by sensor M1 is thus filtered by the filters FILT 20 and FILT 21 then phase shifted by DPH 30 and amplified by AMPL 40. This chain forms an oscillator whose frequency is characteristic of that of the resonance of the work piece 1 if the central frequency of the filters is centered on the frequency of the selected resonance of the workpiece 1 and if the phase of the whole chain has been compensated for by the phase shifter DEPH 30. A microcomputer 60 or microprocessor is connected conventionally to the controls of selectors SELE 10 and SELS 12 so as to choose one of the resonance modes, on our example described it allows a choice between the horizontal and vertical modes depending on whether contacts a or b are closed.

The microprocessor 60 is also connected to the programming controls of filters FILT 20 and FILT 21 through the connection 71, which allows one of the frequencies to be selected from the set of frequencies of the work piece 1.

The microprocessor 60 is connected to the phase control of the programmable phase shifter DEPH 30, by the control 72, which allows the phase shifts of the different elements of the chain to be compensated for, which phase shifts are caused in particular by the propagation time of sound in air, through the sensor and through the exciter concerned.

A frequency meter 80 has its input connected for example to the output of the filter FILT 21 and its output 73 connected to the microprocessor 60. The microprocessor 60 is connected (connection 75) to a D-A converter CNA 90 whose output 74 is connected to the level control of the amplifier AMPL 40. This microprocessor 60 is further connected to the output of an A-D converter CAN 91 through the connection 76, whose input is connected to the output 51 of the first filter FILT 20, which allows a rapid rise of the vibration level to be programmed by programming at the beginning of a measuring cycle excitation of high amplitude, then when the vibration level of the work piece 1 measured by the CAN 91 is sufficient, the microprocessor 60 reduces the level of the excitation. This forms a control of the level of vibration of work piece 1 so as to obtain a sufficiently high sound level so as to be able to measure the frequency but limited so as to pass rapidly to the next measurement at another resonance frequency.

The control 77 of the selector SELO 11 is connected to the microprocessor 60. In FIG. 2, this selector 11 is shown in the closed position on the input terminal a which allows a looped chain to be obtained during the frequency measurement.

In order to facilitate start up of the oscillations and so to accelerate the measuring rates, the input terminal b of the selector SELO 11 is connected during this start up phase to the output 53 of filter FILT 21 whereas terminal a is disconnected. Because of this operation, the filter FILT 21 thus forms an oscillator whose amplified output signal will excite the work piece 1 and help in starting up the oscillations. As soon as the level measured by the A-D converter CAN 91 is sufficiently high, SELO 11 is set back to its first position. This operation avoids using an auxiliary generator. The two solutions may both be envisaged.

The microprocessor 60 programs the successive frequencies as a function of the previously chosen modes of the filters FILT 20 and 21, the phase of the phase shifter DEPH 30 and causes acquirement of the different resonance frequencies by the frequency meter 80 for the different exciter and sensor pairs concerned. The set of measurement results is then processed by the computer using a mathematical model which is specific to each type or series of work pieces. To this microprocessor 60 are conencted the usual peripherals (screen, keyboard, memories..) which have not been shown in these Figs.

This mathematical model has been previously determined on a first batch of work pieces whose characteristic parameters are measured by usual methods, for example the coefficient of elasticity, the weight, the localized defects.

Using the apparatus, the resonance frequencies are measured. By means of a statistical method, for example a linear regression method, the coefficients are determined of a four linear equation system of the type:

$$df1 = a11*dE + a12*dP + a13*dD1 + a14*dD2$$

$$df2 = a21*dE + a22*dP + a23*dD1 + a24*dD2$$

$$df3 = a31*dE + a32*dP + a33*dD1 + a34*dD2$$

$$df4 = a41*dE + a42*dP + a43*dD1 + a44*dD2$$

where df1 or df4 represent the frequency differences with respect to the nominal frequencies of four resonance modes, dE, dP, dD1, represent the differences of the characteristics of a work piece 1 for example respectively the differences in the module of elasticity, the weight differences, a first localized defect, a second localized defect, all to a44 represent the sensitivity coefficients of each characteristic of the work piece 1 for one of the resonance frequencies. This equation system may be represented in the form of a matrix by:

$$\begin{matrix} df1 \\ df2 \\ df3 \\ df4 \end{matrix} = \begin{matrix} a11 & a12 & a13 & a14 \\ a21 & a22 & a23 & a24 \\ a31 & a32 & a33 & a34 \\ a41 & a42 & a43 & a44 \end{matrix} * \begin{matrix} dE \\ dP \\ dD1 \\ dD2 \end{matrix}$$

that is (FREQUENCY VECTOR)=(MATRIX aij) * (WORK PIECE VECTOR). By suitably choosing the resonance frequency modes, it is possible to obtain a non degenerated matrix aij which is reversible: (MATRIX bij)=reverse (MATRIX aij).

Whence the equation (2): (WORK PIECE CHARACTERISTICS VECTOR)=(MATRIX bij) * (FREQUENCY VECTOR). Namely the equation (3):

$$\begin{matrix} dE \\ dP \\ dD1 \\ dD2 \end{matrix} = \begin{matrix} b11 & b12 & b13 & b14 \\ b21 & b22 & b23 & b24 \\ b31 & b32 & b33 & b34 \\ b41 & b42 & b43 & b44 \end{matrix} * \begin{matrix} df1 \\ df2 \\ df3 \\ df4 \end{matrix}$$

We are then in possession of the element allowing starting up of the series testing. The testing apparatus measures for each work piece 1 the resonance frequencies of the differences df1 to df4, it uses the equation system (3) for obtaining the characteristics dE, dP, dD1, dD2, which are compared with thresholds established at the request of the user for accepting or refusing the work piece 1.

In this example, we have shown a four equation system with four unknowns, but the reasoning is identical for systems of different orders.

The apparatus may be coupled to an automatic device for loading and ejecting work pieces for allowing mass production testing.

I claim:

1. A defect detection apparatus for detecting defects in work pieces, comprising a plurality of excitation means for exciting vibrations in a workpiece and a plurality of sensors for sensing vibrations emitted by a work piece whose sound resonance frequencies it is desired to measure so as to evaluate the quality thereof; a first selection means for selecting one of the sensors, an output of said first selection means being connected to filtering means an output of said filtering means connecting to a phase shift means, an output of said phase shift means connected to an amplification means, an output of said amplification means connected to a second selection means; and an output of the second selection means being connected to each excitation means for exciting the work piece whereby the apparatus permits a sustained oscillation to be obtained from the workpiece so as to permit the measurement of the frequency thereof by means of a frequency meter.

2. A defect detection apparatus according to claim 1, characterized in that the filtering means and the phase shift means are programmable and are controlled by a microprocessor which allows different resonance modes of the work piece to be selected in turn and in that the frequency meter is connected to the microprocessor for acquiring the characteristic frequency of each resonance mode.

3. Defect detection apparatus according to claim 1, characterized in that the amplification means is level programmable.

4. Defect detection apparatus according to claim 3, characterized in that the programmable level of said amplification means is measured and is used for controlling the level of the excitation means.

5. Defect detection apparatus according to claim 2, characterized in that the filtering means comprises a plurality of filters and one of the filters is relooped on itself through a selector controlled by the microprocessor.

* * * * *

UNITED STATES PATENT AND TRADEMARK OFFICE
CERTIFICATE OF CORRECTION

PATENT NO. : 4,829,823
DATED : May 16, 1989
INVENTOR(S) : Michel Jacob

It is certified that error appears in the above-identified patent and that said Letters Patent is hereby corrected as shown below:

On the title page:

item [19] line 2, change "Michel" to -- Jacob --;

left column, after "[76] Inventor:", change "Jacob Michel" to -- Michel Jacob --.

Signed and Sealed this

Tenth Day of July, 1990

Attest:

HARRY F. MANBECK, JR.

Attesting Officer

Commissioner of Patents and Trademarks